US008951238B2

(12) United States Patent
Takahashi et al.

(10) Patent No.: US 8,951,238 B2
(45) Date of Patent: Feb. 10, 2015

(54) ABSORBENT PRODUCT AND DISPOSABLE DIAPER

(75) Inventors: Yuki Takahashi, Mima-Gun (JP); Emi Amano, Mima-Gun (JP)

(73) Assignee: Livedo Corporation, Shikokuchuo-shi (JP)

( * ) Notice: Subject to any disclaimer, the term of this patent is extended or adjusted under 35 U.S.C. 154(b) by 142 days.

(21) Appl. No.: 13/883,740

(22) PCT Filed: Nov. 7, 2011

(86) PCT No.: PCT/JP2011/006211
§ 371 (c)(1),
(2), (4) Date: May 6, 2013

(87) PCT Pub. No.: WO2012/063461
PCT Pub. Date: May 18, 2012

(65) Prior Publication Data
US 2013/0226126 A1 Aug. 29, 2013

(30) Foreign Application Priority Data
Nov. 10, 2010 (JP) ................................. 2010-252162

(51) Int. Cl.
*A61F 13/494* (2006.01)
(52) U.S. Cl.
CPC ..... *A61F 13/49426* (2013.01); *A61F 13/49413* (2013.01)
USPC .................................................. 604/385.28
(58) Field of Classification Search
USPC ...................... 604/385.23, 385.248
See application file for complete search history.

(56) References Cited

U.S. PATENT DOCUMENTS

| | | | | | |
|---|---|---|---|---|---|
| 4,935,021 | A | * | 6/1990 | Huffman et al. | 604/385.26 |
| 5,746,732 | A | * | 5/1998 | Olsson et al. | 604/385.28 |
| 6,156,024 | A | * | 12/2000 | Schulte et al. | 604/385.28 |
| 6,423,045 | B1 | * | 7/2002 | Wise et al. | 604/385.12 |
| 2001/0014797 | A1 | * | 8/2001 | Suzuki et al. | 604/378 |
| 2002/0055726 | A1 | * | 5/2002 | Costa | 604/358 |

(Continued)

FOREIGN PATENT DOCUMENTS

| CN | 1360883 A | 7/2002 |
|---|---|---|
| CN | 2598538 Y | 1/2004 |

(Continued)

OTHER PUBLICATIONS

International Search Report PCT/JP2011/006211, Mailing Date of Feb. 29, 2012.

*Primary Examiner* — Susan Su
(74) *Attorney, Agent, or Firm* — Westerman, Hattori, Daniels & Adrian, LLP (57) ABSTRACT

An absorbent body of a diaper has a central absorbent core, a pair of side absorbent cores and a pair of side elastic members. The side elastic members lie left and right of a front portion of the central absorbent core. The side absorbent cores lie left and right of rear and middle portions of the central absorbent core. In the diaper, by contraction of the side elastic members, the side absorbent cores come into close contact with the insides of thighs of a wearer, and urine is prevented from leaking from leg circumferences. Since the side absorbent cores are positioned left and right of the rear and middle portions of the central absorbent core, portions of the wearer's leg circumferences in the vicinity of the front are not covered with the side absorbent cores, and interference with leg movement of the wearer is prevented.

12 Claims, 4 Drawing Sheets

(56) References Cited

U.S. PATENT DOCUMENTS

| | | | |
|---|---|---|---|
| 2002/0087140 A1* | 7/2002 | Otsubo | 604/385.28 |
| 2002/0123732 A1* | 9/2002 | Koyama et al. | 604/385.24 |
| 2003/0004483 A1* | 1/2003 | Otsubo | 604/385.01 |
| 2003/0009143 A1 | 1/2003 | Ludwig et al. | |
| 2003/0023225 A1* | 1/2003 | Sayama | 604/385.28 |
| 2003/0135177 A1* | 7/2003 | Baker | 604/368 |
| 2004/0006325 A1 | 1/2004 | Minato | |
| 2004/0030317 A1 | 2/2004 | Torigoshi | |
| 2004/0133181 A1 | 7/2004 | Ishiguro et al. | |
| 2005/0010188 A1 | 1/2005 | Glaug et al. | |
| 2005/0171500 A1* | 8/2005 | Koyama et al. | 604/385.28 |
| 2007/0088309 A1* | 4/2007 | Ehrnsperger et al. | 604/385.28 |
| 2007/0156108 A1* | 7/2007 | Becker et al. | 604/372 |
| 2010/0228210 A1* | 9/2010 | Busam et al. | 604/366 |
| 2012/0323195 A1* | 12/2012 | Ehrnsperger et al. | 604/366 |

FOREIGN PATENT DOCUMENTS

| | | |
|---|---|---|
| CN | 1480115 A | 3/2004 |
| EP | 1219273 A2 | 3/2002 |
| JP | 2002-209939 A | 7/2002 |
| JP | 2002-360629 A | 12/2002 |
| JP | 2003-275236 A | 9/2003 |
| JP | 2004-049707 A | 2/2004 |
| JP | 2004-049709 A | 2/2004 |
| JP | 2004-049764 A | 2/2004 |
| JP | 2004-105704 A | 4/2004 |
| JP | 2004-305601 A | 11/2004 |
| JP | 2007-222370 A | 9/2007 |
| JP | 2007-229198 A | 9/2007 |
| JP | 2010-184134 A | 8/2010 |
| KR | 10-2002-0055367 A | 7/2002 |
| KR | 10-2004-0010324 A | 1/2004 |
| WO | 02/43636 A1 | 6/2002 |

* cited by examiner

ABSORBENT PRODUCT AND DISPOSABLE DIAPER

TECHNICAL FIELD

The present invention relates to an absorbent product for receiving excrement from a wearer and a disposable diaper.

BACKGROUND ART

A disposable diaper whose portion to face a crotch portion of a wearer is folded along groins of the wearer is conventionally proposed. A development type disposable diaper disclosed in Japanese Patent Application Laid-Open No. 2007-222370 (Document 1) has a liquid-pervious top sheet, a water-repellent or liquid-impervious back sheet and an absorbent core located between the both sheets. In a crotch region, the absorbent core has a central core and a pair of leg cores positioned at both sides of the central core. Elastic members are provided at intermediate areas between the central core and the pair of leg cores. In the intermediate areas, portions of the top sheet stand up on a skin contact surface so as to form a pair of water-conducting walls. When the disposable diaper is worn, portions provided with the leg cores are bent downward due to existence of the intermediate areas. In the disposable diaper, the portions are brought into close contact with the insides of thighs of the wearer, and therefore leakage from leg circumferences is improved.

A pants-type disposable diaper disclosed in Japanese Patent Application Laid-Open No. 2004-49709 (Document 2) has a top sheet, a back sheet, an absorbent main body located between the both sheets, and leg flap elastic members extending along leg openings of the diaper. In a crotch region, the leg flap elastic members are positioned between the absorbent main body and the back sheet. In the absorbent main body, on each side portion in a width direction, a leg flap absorbent body, which is bending toward an outer surface by extensional stress of the leg flap elastic member, is formed. When the diaper is worn, the leg flap absorbent bodies are brought into contact with the insides of thighs of the wearer, and therefore excrement which has leaked out from the crotch region is absorbed into the leg flap absorbent bodies.

In a disposable diaper disclosed in Japanese Patent Application Laid-Open No. 2002-209939 (Document 3), strip-like leg absorbent bodies are provided left and right of a central absorbent body, and intermediate areas where no absorbent body is provided or a weight of absorbent body per unit area is low are provided between the central absorbent body and the leg absorbent bodies. In addition, elastic members are fixed between the leg absorbent bodies and a back sheet.

In the diaper of Document 1, since the portions provided with the leg cores are brought into close contact with large areas of leg circumferences of the wearer, they interfere with leg movement of the wearer. The same applies to Documents 2 and 3.

SUMMARY OF INVENTION

The present invention is intended for an absorbent product for receiving excrement from a wearer. It is an object of the present invention to bring the absorbent product into close contact with leg circumferences (portions of leg circumferences) without interfering with leg movement of the wearer.

The absorbent product according to the present invention comprises: a central absorbent core to face a crotch portion of a wearer; a pair of side absorbent cores extending in a front-rear direction from left and right sides of a rear portion of the central absorbent core to left and right sides of a middle portion thereof; a back sheet covering outer surfaces of the central absorbent core and the pair of side absorbent cores; a top sheet covering inner surfaces of the central absorbent core and the pair of side absorbent cores; and side elastic members lying at left and right sides of a front portion of the central absorbent core and being elasticated in the front-rear direction.

In the present invention, it is possible to bring the absorbent product into close contact with leg circumferences without interfering with leg movement of the wearer.

According to a preferred embodiment of the present invention, since the absorbent product further comprises a pair of crotch elastic members lying between the central absorbent core and the pair of side absorbent cores and extending in the front-rear direction, the side absorbent cores can be brought into closer contact with the leg circumferences.

According to another preferred embodiment of the present invention, since the central absorbent core is formed in a form of hourglass, a portion provided with the central absorbent core can be concave easily and excrement can be received more surely. When a urine receiving pad is used, the urine receiving pad can be easily held.

According to an aspect of the present invention, the absorbent product further comprises a pair of side wall parts lying between the central absorbent core and the pair of side absorbent cores and standing upward from the top sheet. In this case, it is preferred that the top sheet comprises a central top sheet and a pair of side top sheets, an inner surface of the central absorbent core is covered with the central top sheet, inner surfaces of the pair of side absorbent cores are covered with the pair of side top sheets, the pair of side wall parts is formed of a hydrophobic nonwoven fabric(s) which lies from an outer surface of the central absorbent core via both side portions thereof and then stands upward, and the pair of side top sheets is bonded to the pair of side wall parts. Therefore, moisture which has been absorbed in the central absorbent core is prevented from moving to the side absorbent cores.

According to another aspect of the present invention, side portions of the pair of side absorbent cores, which are farther than the other side portions from the central absorbent core, are covered with the top sheet, the absorbent product further comprises an outer surface sheet which is formed of a hydrophobic nonwoven fabric and which lies outside the back sheet, the outer surface sheet protrudes left and right from the side portions of the pair of side absorbent cores. It is therefore possible to prevent moisture from leaking out from the side portions of the side absorbent cores.

The present invention is also intended for a disposable diaper, the disposable diaper comprises: a cover sheet; and the above absorbent product which is attached to the cover sheet.

These and other objects, features, aspects and advantages of the present invention will become more apparent from the following detailed description of the present invention when taken in conjunction with the accompanying drawings.

DESCRIPTION OF EMBODIMENTS

Figure 1:
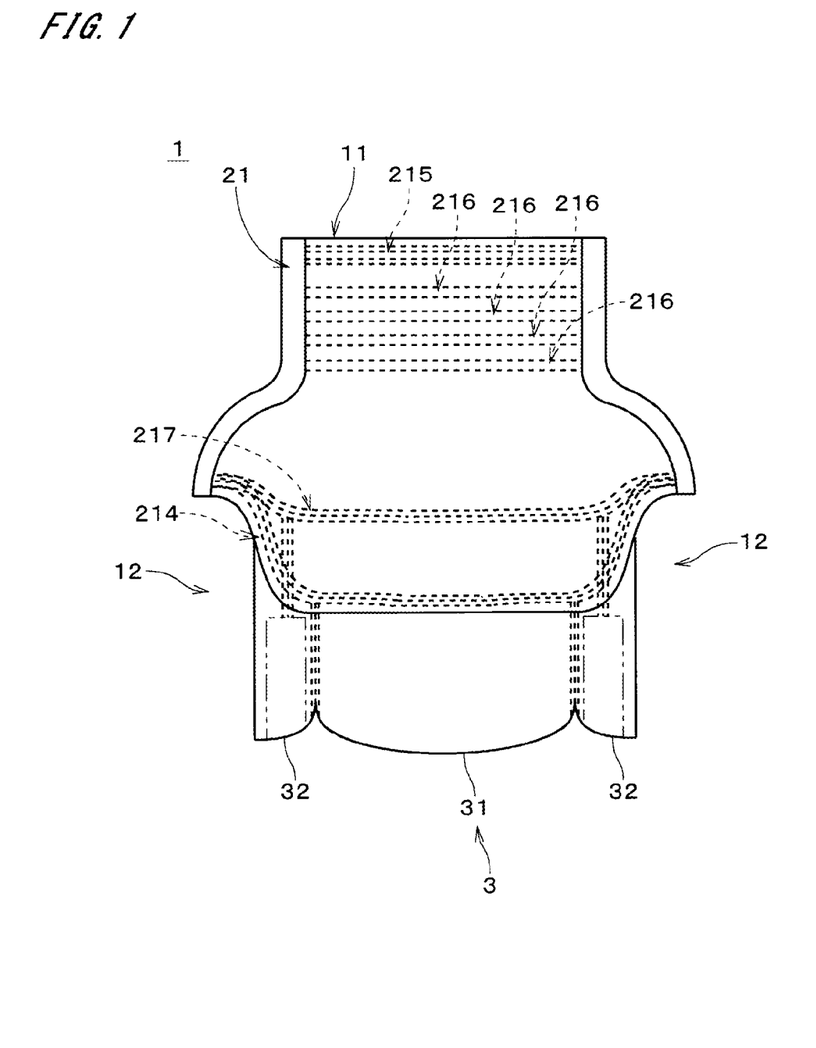
FIG. 1 is a view showing a diaper in accordance with a first preferred embodiment.

FIG. 1 is a front view of a disposable diaper 1 (hereinafter simply referred to as a "diaper 1") in accordance with a first preferred embodiment of the present invention. In FIG. 1, a portion to be positioned on the front side (stomach side) of a wearer is shown. The diaper 1 is a pants-type (i.e., pull-up type) diaper and has a waist opening 11 positioned at an upper part and a pair of leg openings 12 positioned on left and right portions of a lower part.

Figure 2:
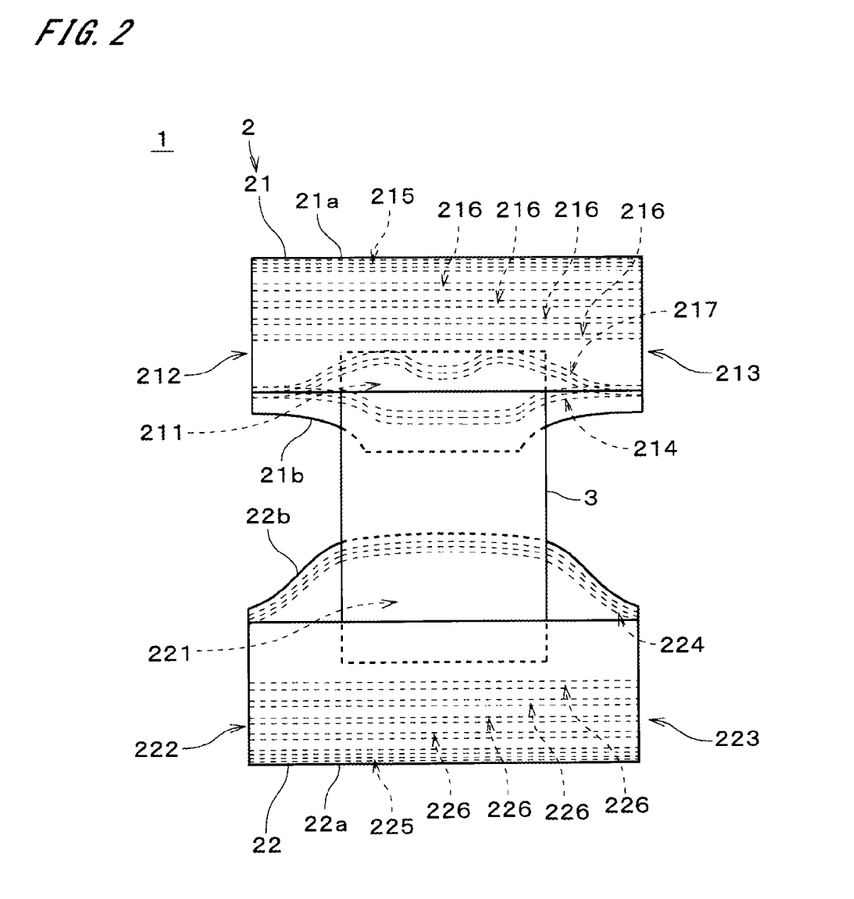
FIG. 2 is a developed view of the diaper.

FIG. 2 is a developed view of the diaper 1, and it shows internal structure of the diaper 1. In FIG. 2, a portion, to face the front side, of the diaper 1 shown in FIG. 1 is shown on the upper side of FIG. 2, and a portion to face the back side is shown on the lower side. The diaper 1 has a cover sheet (outer covering sheet) 2 and an absorbent body 3 which is an absorbent product attached (fixed) to the cover sheet 2. In FIG. 2, only contour of the absorbent body 3 is drawn. In the following description, an upper position in FIG. 2 is represented by "front" in the diaper 1, and a lower portion in FIG. 2 is represented by "rear" in the diaper 1 (i.e., "upward" in FIG. 2 is "frontward" in the diaper 1, and "downward" in FIG. 2 is "rearward" in the diaper 1.). The cover sheet 2 has a front cover sheet 21 to be positioned on skin of the front side of the wearer and a rear cover sheet 22 to be positioned on skin of the back side of the wearer.

Each of the front cover sheet 21 and the rear cover sheet 22 is formed of a plurality of sheets which are laminated. In the front cover sheet 21 and the rear cover sheet 22, a water-repellent and/or liquid-impervious nonwoven fabric made of hydrophobic fibers, or a plastic film is used. A laminated sheet of the nonwoven fabric and the plastic film may be used. It is preferable that a plastic film with permeability (breathability) is used. Furthermore, there may be a case where a liquid-pervious nonwoven fabric made of hydrophobic fibers where hydrophilic treatment is performed, or a nonwoven fabric made of hydrophilic fibers is used for the front cover sheet 21 and the rear cover sheet 22.

In the diaper 1, left and right end portions 212, 213 of the front cover sheet 21 shown in FIG. 2 are bonded to left and right end portions 222, 223 of the rear cover sheet 22 by heat-sealing or the like, to form the waist opening 11 and the leg openings 12 shown in FIG. 1.

The absorbent body 3 is positioned between the front cover sheet 21 and the rear cover sheet 22. A front portion of the absorbent body 3 is bonded on a portion, close to the rear cover sheet 22, in a middle portion 211 of the front cover sheet 21 in the left-right direction in FIG. 2, that is, bonded on a middle lower part of the front cover sheet 21 when the diaper 1 is in the form of pants. A rear portion of the absorbent body 3 is bonded on a portion, close to the front cover sheet 21, in a middle portion 221 of the rear cover sheet 22 in the left-right direction, that is, bonded on a middle lower part of the rear cover sheet 22 when the diaper 1 is in the form of pants. As shown in FIG. 1, the absorbent body 3 protrudes downward from lower portions of the front cover sheet 21 and the rear cover sheet 22.

When the diaper 1 is worn, the absorbent body 3 lies from the middle portion 211 of the front cover sheet 21 via the crotch portion of the wearer to the middle portion 221 of the rear cover sheet 22, to receive excrement from the wearer.

The front cover sheet 21 has a leg elastic member 214, a waist elastic member 215, body-fitting elastic members 216 (i.e., elastic members to bring the diaper 1 into close contact with the body of the wearer) and an auxiliary elastic member 217 each of which is formed of a plurality of polyurethane yarns, and each elastic member 214 to 217 is located and bonded between the plurality of sheets in the front cover sheet 21 with hot melt adhesive in a state where the elastic member 214 to 217 is stretched (in stretched state). The leg elastic member 214 is provided along an edge (rear edge) 21*b* lying on the rear of the front cover sheet 21 in the front-rear direction, that is, provided along the lower edge in FIG. 1. The waist elastic member 215 extends along an edge (front edge) 21*a* lying on the front of the front cover sheet 21 in the front-rear direction, that is, along the upper edge in FIG. 1 in a linear fashion. The plurality of body-fitting elastic members 216, lying between the waist elastic member 215 and the leg elastic member 214, extend in parallel with the waist elastic member 215. The auxiliary elastic member 217, lying between the leg elastic member 214 and the body-fitting elastic members 216, windingly extends in the left-right direction of FIG. 2.

The rear cover sheet 22 has a leg elastic member 224, a waist elastic member 225 and body-fitting elastic members 226 each of which is formed of a plurality of polyurethane yarns, and each elastic member 224 to 226 is located and bonded between the plurality of sheets in the rear cover sheet 22 with hot melt adhesive in a state where the elastic member 224 to 226 is stretched. The leg elastic member 224 is provided along an edge (front edge) 22*b* lying on the front of the rear cover sheet 22 in the front-rear direction, that is, provided along the lower edge in FIG. 1. The waist elastic member 225 extends along an edge (rear edge) 22*a* lying on the rear of the rear cover sheet 22 in the front-rear direction, that is, along the upper edge in FIG. 1 in a linear fashion. The plurality of body-fitting elastic members 226, lying between the waist elastic member 225 and the leg elastic member 224, extend in parallel with the waist elastic member 225.

As shown in FIGS. 1 and 2, in the diaper 1, the leg elastic members 214, 224 of the front cover sheet 21 and the rear cover sheet 22 and after-mentioned crotch elastic members of the absorbent body 3 contract to form leg gathers, and the leg gathers are in close contact with the vicinity of the groins of the wearer (the bases of the legs) when the diaper 1 is worn. By providing the auxiliary elastic member 217, portions around leg circumferences in the front of the diaper 1 are strengthened. Actually, portions of the leg elastic members 214, 224 and the auxiliary elastic member 217 which overlap with the absorbent body 3 are cut to pieces, and the portions have no elastic properties. Furthermore, the waist elastic members 215, 225 and the body-fitting elastic members 216, 226 contract to form waist gathers, and the diaper 1 is in close contact with the waist of the wearer.

Figure 3:
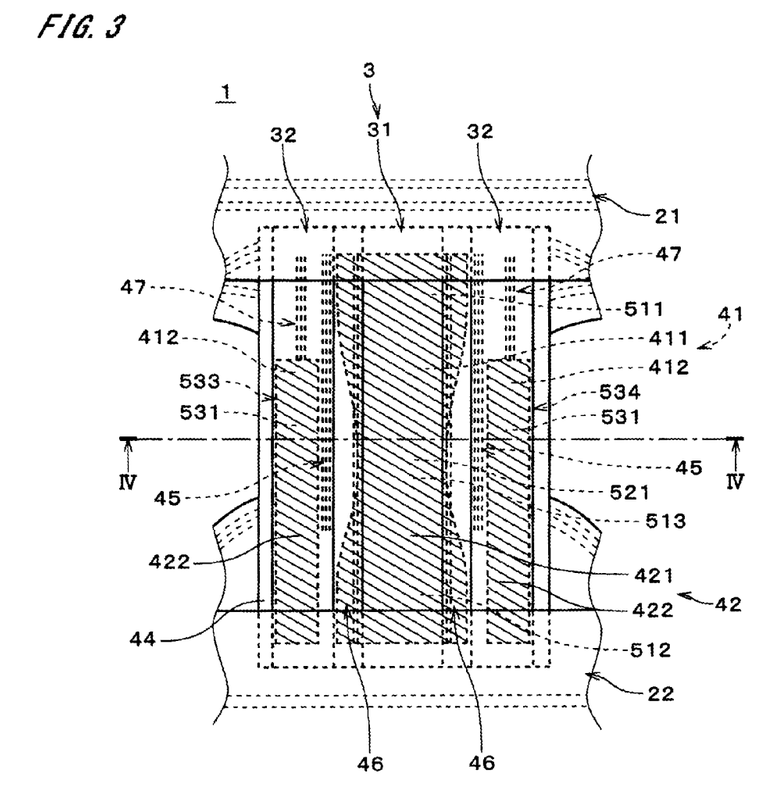
FIG. 3 is a plan view of an absorbent body.
Figure 4:
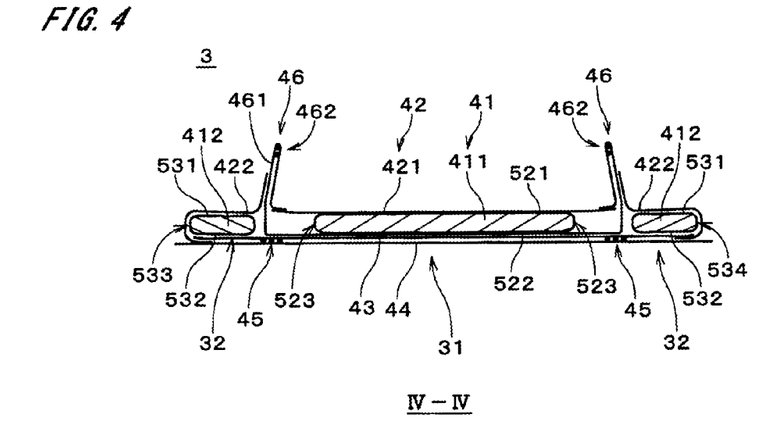
FIG. 4 is a cross-sectional view of the absorbent body.

FIG. 3 is an enlarged view showing the vicinity of the absorbent body 3 in FIG. 2. FIG. 4 is a cross-sectional view of the absorbent body 3 taken along a line Iv-Iv in FIG. 3. In FIG. 4, respective constituents of the absorbent body 3 are drawn so as to be slightly apart from one another for the convenience of illustration. The same applies to after-mentioned FIG. 5. The absorbent body 3 has an absorbent core 41, a top sheet 42 to lie between the absorbent core 41 and the wearer, a back sheet 43 (shown only in FIG. 4) covering one surface of the absorbent core 41 which is different from a surface facing the top sheet 42, and an outer surface sheet covering the back sheet 43. The absorbent body 3 further has a pair of crotch elastic members 45 extending in the front-rear direction of FIG. 3, that is, in a direction orthogonal to the paper of FIG. 4, a pair of side wall parts 46 standing upward from the top sheet 42, and a pair of side elastic members 47 (shown only in FIG. 3) extending in the front-rear direction.

The absorbent core 41 has a central absorbent core 411 to face the crotch portion of the wearer, and a pair of side absorbent cores 412 provided left and right of the central absorbent core 411 (i.e., the side absorbent cores 412 are located to the left and right of the central absorbent core 411, respectively.). In FIG. 3, hatching lines are drawn at the central absorbent core 411 and the side absorbent cores 412. Each of the central absorbent core 411 and the side absorbent cores 412 is formed by wrapping a mixture of hydrophilic fibers such as crushed pulp fibers or cellulose fibers and super absorbent material such as granulated super absorbent polymers or super absorbent fibers, in a tissue paper, a liquid-pervious nonwoven fabric or the like. The tissue paper, the liquid-pervious nonwoven fabric or the like is bonded to the hydrophilic fibers and the absorbent material with hot melt adhesive. Therefore, deformation of the hydrophilic fibers and falling of the absorbent material (especially, falling after absorption of moisture) are prevented.

As shown in FIG. 3, the central absorbent core 411 is formed in a form of hourglass (sandglass), and widths of a portion 511 overlapping with the front cover sheet 21 and a portion 512 overlapping with the rear cover sheet 22 are larger than that of a portion 513 positioned to face the crotch portion of the wearer. Hereinafter the portions 511 to 513 are referred to as a "front portion 511", a "rear portion 512" and a "middle portion 513" of the central absorbent core 411, respectively.

In the diaper 1, a front end portion of the absorbent body 3 is bonded to the front cover sheet 21 so as to be located between its sheets. Similarly, a rear end portion of the absorbent body 3 is bonded to the rear cover sheet 22 so as to be located between its sheets. Therefore, peeling of the front and rear end portions of the absorbent body 3 is prevented. Out of sheets included in each of the front cover sheet 21 and the rear cover sheet 22, a sheet in contact with an inner surface of the absorbent body 3 overlaps with the absorbent body 3 by a shorter distance in the front-rear direction than that of a sheet in contact with an outer surface of the absorbent body 3.

The side absorbent cores 412 are long in the front-rear direction, and lengths of the side absorbent cores 412 are shorter than that of the central absorbent core 411. The side absorbent cores 412 exists so as to extend in the front-rear direction from left and right sides of the rear portion 512 of the central absorbent core 411 to left and right sides of the middle portion 513 thereof (i.e., from positions by the rear portion 512 to positions by the middle portion 513). In other words, the side absorbent cores 412 have shapes where portions positioned left and right of the front portion 511 of the central absorbent core 411 are lacking. The front portion 511, the middle portion 513 and the rear portion 512 of the central absorbent core 411 do not have to be distinguished exactly from one another, and a middle area being comparatively long in the front-rear direction may be treated as a middle portion 513. The lengths of the side absorbent cores 412 are appropriately determined as long as they can reduce interference with walking by the wearer as described later.

As shown in FIGS. 3 and 4, the top sheet 42 has a strip-like central top sheet 421 and a pair of strip-like side top sheets 422 positioned left and right of the central top sheet 421. The central top sheet 421 and the side top sheets 422 are made of liquid-pervious sheet material, for example they are nonwoven fabrics made of hydrophilic fibers. The nonwoven fabrics used as the central top sheet 421 and the side top sheets 422 are for example spunbond nonwoven fabrics, point-bond nonwoven fabrics, air-through nonwoven fabrics or spunlace nonwoven fabrics, and as hydrophilic fibers for making these nonwoven fabrics, normally, cellulose, rayon, cotton and the like are used. There may be a case where liquid-pervious nonwoven fabrics made of hydrophobic fibers (polypropylene, polyethylene, polyester, polyamide, nylon or the like) where hydrophilic treatment is performed on those surfaces with surfactant are used as the central top sheet 421 and the side top sheets 422.

The central top sheet 421 covers an inner surface 521 of the central absorbent core 411 shown in FIG. 3, that is, the surface 521 facing up in FIG. 4. The surface 521 is a surface in contact with skin of the wearer when the diaper 1 is worn, and hereinafter the surface 521 is referred to as the "inner surface 521". And another surface of the central absorbent core 411 opposite to the inner surface 521 is referred to as an "outer surface 522". In a planar view, a portion of the absorbent body 3 where the central top sheet 421 exists is referred to as a "central absorbent part 31".

The left side top sheet 422 (i.e., the side top sheet 422 on the left side) covers an inner surface 531 of the left side absorbent core 412 shown in FIG. 3, that is, the surface 531 facing up in FIG. 4, and its left side portion 533. Surfaces 531 of the both side absorbent cores 412 are surfaces in contact with skin of the wearer when the diaper 1 is worn, and hereinafter the surfaces 531 are referred to as "inner surfaces 531". Surfaces of the side absorbent cores 412 opposite to the inner surfaces 531 are referred to as "outer surfaces 532". The right side top sheet 422 (i.e., the side top sheet 422 on the right side) covers the inner surface 531 of the right side absorbent core 412 and its right side portion 534. In the following description, portions of the absorbent body 3 where the pair of side top sheets 422 exists in a planar view are referred to as "side absorbent parts 32".

As shown in FIG. 4, the pair of side wall parts 46 lies between the central absorbent core 411 and the pair of side absorbent cores 412, and has a hydrophobic nonwoven fabric 461 (exactly parts of the fabric) and a pair of elastic members 462. The hydrophobic nonwoven fabric 461 covers the outer surface 522 and the left and right side portions 523 of the central absorbent core 411. Furthermore, both end portions of the hydrophobic nonwoven fabric 461 in the left-right direction extend upward in FIG. 4 and turn down (are folded back) toward the central top sheet 421. Both end, in the front-rear direction, of the end portions are bonded on the central top sheet 421.

Figure 5:
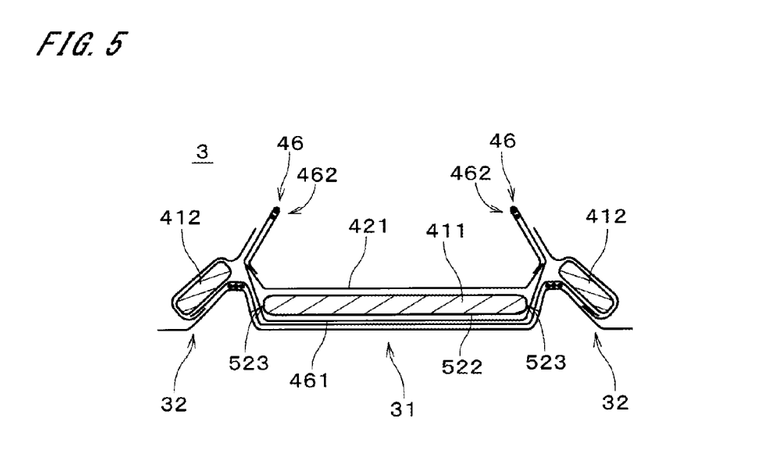
FIG. 5 is a cross-sectional view of the absorbent body.

The elastic members 462 extend in the front-rear direction, and are bonded on the insides of turndown portions of the hydrophobic nonwoven fabric 461 with hot melt adhesive or the like. The side top sheets 422 are bonded on outward-facing surfaces of the side wall parts 46 in the left-right direction. As shown in FIG. 5, the side wall parts 46 are inwardly inclined toward the central absorbent core 411 by contraction of the elastic members 462, and come into contact with the vicinity of the groins of the wearer (the bases of the legs). The side wall parts 46 prevent lateral leakage of excrement.

As shown in FIG. 4, the back sheet 43 covers the outer surface 522 of the central absorbent core 411 and the outer surfaces 532 of the side absorbent cores 412 with intervening hydrophobic nonwoven fabric 461. For the back sheet 43, used is a water-repellent and/or liquid-impervious nonwoven fabric (for example, a spunbond nonwoven fabric, meltblown nonwoven fabric or SMS (spunbond-meltblown-spunbond) nonwoven fabric) made of hydrophobic fibers, or a water-repellent and/or liquid-impervious plastic film. A laminated sheet of the nonwoven fabric and the plastic film may be used. In the diaper 1, the back sheet 43 prevents moisture of urine or the like from leaking (exuding) outside the absorbent body 3. In a case where a plastic film is used for the back sheet 43, it is preferable that a plastic film with permeability (or breathability) is used, from the view point of preventing sweatiness in the diaper 1 and providing comfortable feeling to the wearer.

An outer surface sheet 44 formed of a hydrophobic nonwoven fabric is provided outside the back sheet 43. The outer surface sheet 44 slightly protrudes left and right in FIGS. 3 and 4 from the left side portion 533 of the left side absorbent core 412 and the right side portion 534 of the right side absorbent core 412, that is, the side portions 533, 534 of the pair of side absorbent cores 412, which are farther than the other side portions from the central absorbent core 411.

As shown in FIG. 3, the side elastic members 47 are provided in front of the side absorbent cores 412, that is, at left and right sides of the front portion 511 of the central absorbent core 411. Each of the side elastic members 47 is formed of a plurality of polyurethane yarns and elasticated in the front-rear direction (i.e., the side elastic members 47 have elastic properties.). Rear ends of the side elastic members 47 are close to the side absorbent cores 412 or overlapped with the side absorbent cores 412, and the side elastic members 47 exert tension in the front-rear direction on the side absorbent cores 412. It is therefore possible to stabilize the form of the side absorbent cores 412 when the diaper 1 is worn.

The crotch elastic members 45 are provided between the central absorbent core 411 and the side absorbent cores 412. Each of the crotch elastic members 45 is formed of a plurality of polyurethane yarns and elasticated in the front-rear direction in a similar fashion to the side elastic members 47.

In the diaper 1, by contraction of the crotch elastic members 45, gathers are formed between the central absorbent core 411 and the side absorbent cores 412. Therefore, as shown in FIGS. 1 and 5, a middle portion of the central absorbent part 31 in the front-rear direction, that is, its lower portion becomes a concave shape depressed downward. Middle portions, in the front-rear direction, of the left and right side absorbent parts 32 are inclined outward and obliquely toward the lower left and the lower right, respectively. When the diaper 1 is worn, the side absorbent parts 32 come into contact with the insides of thighs of the wearer. Portions of the outer surface sheet 44 shown in FIG. 3 which are overlapped with the side absorbent cores 412 are not bonded to the front cover sheet 21 and the rear cover sheet 22 except for the front and rear end portions. Thus, the side absorbent parts 32 are easily inclined outward and downward.

When moisture such as urine is excreted from the wearer, the moisture passes through the central top sheet 421 shown in FIG. 5 and is absorbed into the central absorbent core 411. In the absorbent body 3, the hydrophobic nonwoven fabric 461 of the side wall parts 46 covers the outer surface 522 and the both side portions 523 of the central absorbent core 411, and therefore the moisture is retained in the central absorbent part 31 at a certain level.

When a lot of moisture is excreted, some moisture which has flowed over the side wall parts 46 and leaked outward in the left-right direction from the central absorbent part 31 is absorbed into the side absorbent cores 412 extending in the front-rear direction. As above, in the diaper 1, since the side absorbent parts 32 is provided, leakage of urine or the like from leg circumferences is prevented more effectively.

As structure of the diaper 1 in accordance with the first preferred embodiment have been discussed above, in the diaper 1, the side absorbent cores 412 lie left and right of only the rear portion 512 and the middle portion 513 of the central absorbent core 411 and the side absorbent cores 412 do not exist left and right of the front portion 511. Therefore, portions of the wearer's leg circumferences in the vicinity of the front of the diaper 1 are not covered with the side absorbent cores 412, a cumbersome portion at the leg circumferences is eliminated and interference with leg movement of the wearer is prevented when walking. In the diaper 1, it is more preferred that the side absorbent cores 412 do not overlap with (do not exist on) the front cover sheet 21. Therefore, interference with leg movement of the wearer is prevented more effectively. Since the side elastic members 47 expand and contract, the side absorbent cores 412 can be brought into close contact with the leg circumferences (especially groins). Since the crotch elastic members 45 are provided, the side absorbent parts 32 are inclined so as to be along the insides of thighs of the wearer, and therefore the side absorbent cores 412 can be brought into closer contact with the leg circumferences (portions of leg circumferences).

In the absorbent body 3, since the central absorbent core 411 is formed in a form of hourglass, the central absorbent part 31 easily becomes concave by contraction of the crotch elastic members 45. Thus, excrement can be received more surely. When a urine receiving pad is mounted (attached) on the diaper 1, the urine receiving pad can be easily held (housed) in the central absorbent part 31 because the central absorbent part 31 is concave. In the absorbent body 3, the outer surface sheet 44 protrudes left and right from the side portions 533, 534 of the pair of side absorbent parts 32, which are farther than the other side portions from the central absorbent core 411, and therefore leakage of moisture from the side portions 533, 534 is further suppressed.

The hydrophobic nonwoven fabric 461 forming the side wall parts 46 lies from the outer surface 522 of the central absorbent core 411 via both side portions 523 thereof and then stands upward. Thus, moisture which has been absorbed in the central absorbent core 411 is prevented from moving to the side absorbent cores 412.

In the case where absorbing ability of the side absorbent cores 412 is aggressively utilized while movement of moisture to the side absorbent cores 412 is suppressed to a certain level, a hydrophobic nonwoven fabric which has liquid-pervious properties at some level may be used as the hydrophobic nonwoven fabric 461. In this case, some of moisture absorbed in the central absorbent core 411 gradually penetrates to the side absorbent parts 32 through the liquid-pervious hydrophobic nonwoven fabric to be absorbed in the side absorbent cores 412. Instead of the hydrophobic nonwoven fabric 461, a hydrophilic nonwoven fabric may be used. In the case where the side wall parts 46 are formed with a liquid-pervious hydrophobic nonwoven fabric or hydrophilic nonwoven fabric, it is prevented that urine flows in a longitudinal direction along the side wall parts 46 and urine leakage from the front and rear ends of the absorbent body 3 occurs.

Figure 6:
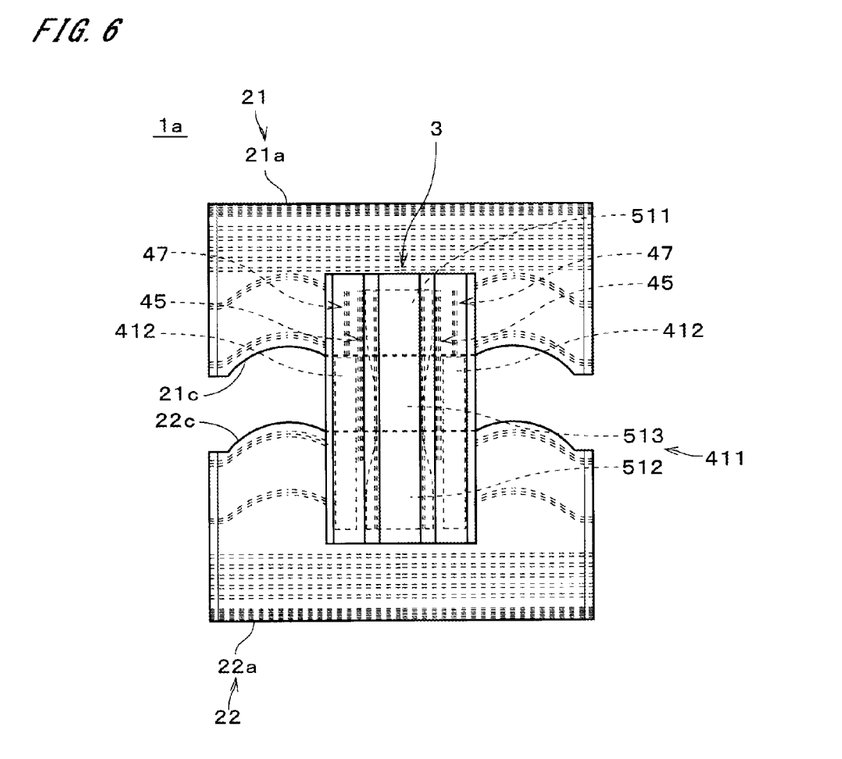
FIG. 6 is a developed view of a diaper in accordance with a second preferred embodiment.

FIG. 6 is a view showing a diaper 1a in accordance with a second preferred embodiment. Structure of the diaper 1a is same as the structure of the diaper 1 shown in FIG. 2 except for shapes of the front cover sheet 21 and the rear cover sheet 22. In the following description, components corresponding to respective components in the diaper 1 are denoted by the same reference signs as the respective components. In the state where the diaper 1a is in the form of pants, a front edge 21a and a rear edge 21c of the front cover sheet 21 in the front-rear direction become an upper edge and a lower edge of the front cover sheet 21, respectively, and a front edge 22c and a rear edge 22a of the rear cover sheet 22 become a lower edge and an upper edge of the rear cover sheet 22, respectively. In the following description, the edge 21a and the edge 21c of the front cover sheet 21 are referred to as the "upper edge 21a" and the "lower edge 21c". Also the edge 22c and the edge 22a of the rear cover sheet 22 are referred to as the "lower edge 22c" and the "upper edge 22a".

In the state where the diaper 1a is developed, as distance in the left-right direction from the absorbent body 3 increases, the lower edge 21c of the front cover sheet 21 goes toward the upper edge 21a of the front cover sheet 21 and then goes away from the upper edge 21a (i.e., the lower edge 21c is oriented (heads) in a direction toward the upper edge 21a and then oriented in a direction away from the upper edge 21a with increasing distance from the absorbent body 3.). In other words, the lower edge 21c of the front cover sheet 21 is concave, in each side of the absorbent body 3 in the left-right direction, so as to be away from the rear cover sheet 22. The lower edge 21c extends almost straight (linearly) in nearly parallel with the left-right direction at an area overlapping with the absorbent body 3.

In the rear cover sheet 22, as distance in the left-right direction from the absorbent body 3 increases, the lower edge 22c goes away from the upper edge 22a of the rear cover sheet 22 and then goes toward the upper edge 22a. In other words, the lower edge 22c of the rear cover sheet 22 is convex toward the front cover sheet 21, in each side of the absorbent body 3 in the left-right direction. The lower edge 22c extends almost straight in nearly parallel with the left-right direction at an area overlapping with the absorbent body 3.

In each of left and right sides of the absorbent body 3 in the diaper 1a, the lower edge 21c of the front cover sheet 21 has an upwardly arched shape (i.e., an edge of portion surrounding leg is formed in concave). Therefore, the lower end portion of the front cover sheet 21 is prevented from interfering with leg movement of the wearer. In each of left and right sides of the absorbent body 3, the lower edge 22c of the rear cover sheet 22 is convex downward, and the lower portions of hips of the wearer (they may include the neighborhoods of the borders between the hips and thighs.) are fully wrapped with the lower end portion of the rear cover sheet 22. Thus, leakage of excrement from the lower portions of hips of the wearer (i.e., leakage of excrement from the rear-lower portion of the diaper 1a) is suppressed.

The front cover sheet 21 and the rear cover sheet 22 are formed by cutting one sheet member along one cutting line, and edges formed by the cutting process become the lower edge 21c of the front cover sheet 21 and the lower edge 22c of the rear cover sheet 22. Thus, in the developed state of the diaper 1a, the lower edge 21c of the front cover sheet 21 has a shape to fit a shape of the lower edge 22c of the rear cover sheet 22 when the front cover sheet 21 and the rear cover sheet 22 are brought close to each other.

Also in the second preferred embodiment, the side absorbent cores 412 lie in left and right sides of only the rear portion 512 and the middle portion 513 of the central absorbent core 411 and the side absorbent cores 412 do not exist in left and right sides of the front portion 511. Therefore, the side absorbent cores 412 are prevented from interfering with leg movement of the wearer. Since the side elastic members 47 are provided, the side absorbent cores 412 can be brought into close contact with leg circumferences. Since the crotch elastic members 45 are provided, the side absorbent cores 412 can be brought into closer contact with the leg circumferences.

Though the preferred embodiments of the present invention have been discussed above, the present invention is not limited to the above-discussed preferred embodiments, but allows various variations.

In the above embodiment, the side elastic members 47 and the crotch elastic members 45 may be formed of strip-like polyurethane films, yarn-like or strip-like natural rubbers, and they may be formed of elastic nonwoven fabrics. In the case where elastic nonwoven fabrics are used as the side elastic members 47, when worn, normally gathers are not formed at areas where the side elastic members 47 exist. If the side absorbent cores 412 are sufficiently tensed (pulled) by the side elastic members 47, the crotch elastic members 45 can be omitted. The leg elastic members 214, 224, the waist elastic members 215, 225, the body-fitting elastic members 216, 226 and the auxiliary elastic member 217 may be formed of strip-like polyurethane films, yarn-like or strip-like natural rubbers or the like.

The central absorbent core 411 and the side absorbent cores 412 may be a continuous member (i.e., a series (string) of members). In this case, thicknesses of portions between the central absorbent core 411 and the side absorbent cores 412 are made small, and therefore the side absorbent cores 412 can be easily inclined downward in the diaper 1. In this instance, the side wall parts 46 are bonded on the top sheet 42.

The hydrophobic nonwoven fabric 461 does not necessarily cover the whole outer surface 522 of the central absorbent core 411. As long as the hydrophobic nonwoven fabric(s) 461 lies at least from portions of the outer surface 522 in the vicinities of the both side portions 523 via the both side portions 523 and then stands upward, moisture which has been absorbed in the central absorbent core 411 is prevented from moving to the side absorbent cores 412. In the absorbent body 3, the side elastic members 47 may be provided so as to be away from the side absorbent cores 412 in the front-rear direction. In this case, since the side top sheets 422 and the back sheet 43 are pulled toward the front of the diaper 1 by the side elastic members 47, the form of the side absorbent cores 412 can be stabilized.

In the above embodiment, the cover sheet 2 may be continuous in the front-rear direction at the crotch region. However, if the cover sheet 2 is divided into the front and rear portions, it is avoided to pull up the side absorbent cores 412 unnecessarily and therefore the side absorbent cores 412 can be an ideal form easily. The absorbent body 3 may be used for another type of disposable diaper other than pants-type diaper, and it may be used, for example an open-type (tape-type) disposable diaper where a portion to be positioned on the front side of a wearer and a portion to be positioned on the back side are fastened with fastening tapes. Structure of the absorbent body 3 may be adapted to another absorbent product such as a urine receiving pad. In a disposable diaper where the absorbent body 3 is attached as a urine receiving pad, it is possible to bring the urine receiving pad into close contact with leg circumferences without interfering with leg movement of the wearer.

The constituent elements of above-discussed preferred embodiments and modified examples may be appropriately combined with one another, as long as they are not mutually exclusive.

While the invention has been shown and described in detail, the foregoing description is in all aspects illustrative and not restrictive. It is therefore understood that numerous modifications and variations can be devised without departing from the scope of the invention.

REFERENCE SIGNS LIST 1, 1a diaper
2 cover sheet
3 absorbent body
21 front cover sheet
22 rear cover sheet
42 top sheet
43 back sheet 44 outer surface sheet
45 crotch elastic member
46 side wall part
47 side elastic member
211 middle portion (of front cover sheet)
212, 213 end portion (of front cover sheet)
221 middle portion (of rear cover sheet)
222, 223 end portion (of rear cover sheet)
411 central absorbent core
412 side absorbent core
421 central top sheet
422 side top sheet
461 hydrophobic nonwoven fabric
511 front portion (of central absorbent core)
512 rear portion (of central absorbent core)
513 middle portion (of central absorbent core)
521 inner surface (of central absorbent core)
522 outer surface (of central absorbent core)
523 side portion (of central absorbent core)
531 inner surface (of side absorbent core)
532 outer surface (of side absorbent core)
533, 534 side portion (of side absorbent core)

The invention claimed is:

1. An absorbent product for receiving excrement from a wearer, the absorbent product having a longitudinal direction and a transverse direction, comprising:
   a central absorbent core to face a crotch portion of a wearer;
   a pair of side absorbent cores comprising a left side absorbent core extending longitudinally from a left side of a rear portion of said central absorbent core to a left side of a middle portion thereof and a right side absorbent core extending longitudinally from a right side of the rear portion of said central absorbent core to a right side of the middle portion thereof;
   a back sheet covering outer surfaces of said central absorbent core and said pair of side absorbent cores;
   a central top sheet covering an inner surface of said central absorbent core:
   a pair of side top sheets covering inner surfaces of said pair of side absorbent cores;
   side elastic members lying at left and right sides of a front portion of said central absorbent core and being elasticated in said longitudinal direction; and
   a pair of side wall parts lying between said central absorbent core and said pair of side absorbent cores and standing upward from said top sheet, wherein
   said pair of side wall parts is formed of a hydrophobic nonwoven fabric(s) which extends between the central absorbent core and each side absorbent core from the outer surface of the central absorbent core to the inner surface of the central absorbent core, and
   said pair of side top sheets is bonded to said pair of side wall parts.

2. The absorbent product according to claim 1, further comprising a pair of crotch elastic members lying between said central absorbent core and said pair of side absorbent cores and extending in said longitudinal direction.

3. The absorbent product according to claim 1, wherein said central absorbent core is formed in a form of hourglass.

4. The absorbent product according to claim 1, wherein
   said pair of side absorbent cores each comprises side portions located transversely farther from a longitudinal centerline of the absorbent product than the side portions of the central absorbent core,
   said absorbent product further comprises an outer surface sheet which is formed of a hydrophobic nonwoven fabric and which lies outside said back sheet,
   said outer surface sheet extends transversely away from the longitudinal centerline beyond said side portions of said pair of side absorbent cores.

5. A disposable diaper, comprising:
   a cover sheet; and
   the absorbent product according to claim 1 which is attached to said cover sheet.

6. The disposable diaper according to claim 5, wherein said cover sheet comprises:
   a front cover sheet; and
   a rear cover sheet whose left and right end portions are bonded to left and right end portions of said front cover sheet;
   said absorbent product is bonded to a middle portion of said front cover sheet in said transverse direction and a middle portion of said rear cover sheet in said transverse direction.

7. A disposable diaper, comprising:
   a cover sheet; and
   the absorbent product according to claim 2 which is attached to said cover sheet.

8. The disposable diaper according to claim 7, wherein said cover sheet comprises:
   a front cover sheet; and
   a rear cover sheet whose left and right end portions are bonded to left and right end portions of said front cover sheet;
   said absorbent product is bonded to a middle portion of said front cover sheet in said transverse direction and a middle portion of said rear cover sheet in said transverse direction.

9. A disposable diaper, comprising:
   a cover sheet; and
   the absorbent product according to claim 3 which is attached to said cover sheet.

10. The disposable diaper according to claim 9, wherein said cover sheet comprises:
    a front cover sheet; and
    a rear cover sheet whose left and right end portions are bonded to left and right end portions of said front cover sheet
    said absorbent product is bonded to a middle portion of said front cover sheet in said transverse direction and a middle portion of said rear cover sheet in said transverse direction.

11. A disposable diaper, comprising:
    a cover sheet; and
    the absorbent product according to claim 4 which is attached to said cover sheet.

12. The disposable diaper according to claim 11, wherein said cover sheet comprises:
    a front cover sheet; and
    a rear cover sheet whose left and right end portions are bonded to left and right end portions of said front cover sheet;
    said absorbent product is bonded to a middle portion of said front cover sheet in said transverse direction and a middle portion of said rear cover sheet in said transverse direction.

* * * * *